United States Patent [19]

Bouisset et al.

[11] Patent Number: 5,075,486

[45] Date of Patent: Dec. 24, 1991

[54] PROCESS FOR PREPARING DI-N-PROPYLACETONITRILE

[75] Inventors: Michel Bouisset, Sisteron; Christian Forqlly, Monein; André Bousquet; Alain Heymes, both of Sisteron, all of France

[73] Assignee: Sanofi, Paris, France

[21] Appl. No.: 584,435

[22] Filed: Sep. 14, 1990

Related U.S. Application Data

[63] Continuation of Ser. No. 242,295, Sep. 9, 1988, abandoned.

[30] Foreign Application Priority Data

Sep. 15, 1987 [FR] France ................................. 87 12773

[51] Int. Cl.$^5$ ............................................ C07C 253/06
[52] U.S. Cl. .................................................. 558/312
[58] Field of Search .......................................... 558/312

[56] References Cited

U.S. PATENT DOCUMENTS

| | | | |
|---|---|---|---|
| 2,904,579 | 9/1959 | Muench et al. | 558/312 |
| 3,256,311 | 6/1966 | Becke et al. | 558/312 |
| 3,514,478 | 5/1970 | Becke et al. | 558/312 |
| 4,315,869 | 2/1982 | Merger et al. | 558/312 |
| 4,436,669 | 3/1984 | Jacques et al. | 558/312 |
| 4,438,042 | 3/1984 | Jacques et al. | 558/312 |
| 4,504,595 | 3/1985 | Jacques et al. | 558/312 X |

*Primary Examiner*—Joseph Paul Brust
*Attorney, Agent, or Firm*—Wegner, Cantor, Mueller & Player

[57] ABSTRACT

The invention relates to the preparation of di-n-propylacetonitrile, according to a process consisting in heating N-(1-propyl-n-butyl)formamide to a temperature of between 350° C. and 550° C. and in the absence of oxygen, in the presence of a catalyst consisting of a silica impregnated with 0.1 to 10% by weight of alkali metal cations.

6 Claims, No Drawings

PROCESS FOR PREPARING DI-N-PROPYLACETONITRILE

This application is a continuation of U.S. application Ser. No. 07/242,295 filed Sept. 9, 1988, now abandoned.

The present invention relates, generally speaking, to a new process for preparing an acetonitrile derivative.

In particular, the invention relates to a new process for preparing di-n-propylacetonitrile of formula:

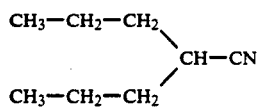

Di-n-propylacetonitrile is a known product which is especially advantageous for the preparation of compounds possessing valuable pharmacological properties. For example, di-n-propylacetonitrile may be used for the preparation of di-n-propylacetamide or "valpromide", or alternatively for the production of di-n-propylacetic acid or "valproic acid", as described in Patents Fr-A-2,383,918 and FR-A-2,383,907.

These compounds are currently widely used on account of their neurotropic properties, and especially on account of their antiepileptic properties.

The traditional processes for preparing di-n-propylacetonitrile are generally complicated, and require the use of reagents which are dangerous to the manufacturing personnel. For example, the preparation of di-n-propylacetonitrile from di-n-propyl ketone makes use of sodium cyanide, an extremely toxic product. In addition, some preparation phases consist of a hydrogenation, which is always difficult to carry out on a large scale.

The search for an industrial process for producing di-n-propylacetonitrile starting, for example, with di-n-propyl ketone, hence remains of fundamental interest.

Processes are already known for preparing aliphatic nitriles from formamide derivatives, by reaction of the latter in the gaseous phase in contact with catalysts, chiefly catalysts based on silica, doped or otherwise. Nevertheless, most of the prior documents relating to these processes specifically describe only the dehydration of formamide derivatives that are incapable either of forming olefins by the breakage of C—N bonds, or of forming isomers.

In this connection, there may be mentioned U.S. Pat. No. 3,256,311, which shows the preparation of aliphatic nitriles from formamides at a temperature of between 460° C. and 560° C. in contact with active silicic acid, or with silicates optionally activated with metal oxides of groups III to VI of the Periodic Classification of the elements, for example titanium oxide. The active silicic acid can, in addition, be combined, if desired, with basic oxides such as calcium oxide, magnesium oxide or aluminium oxide. However, this combination is of no importance. The preparation of acetonitrile from N-methylformamide is specifically described therein, this compound being incapable, however, of forming by-products of the isomeric or ethylenic type.

Similarly, the preparation of aliphatic nitriles, also from formamides, by a dehydration/rearrangement reaction at 400°-650° C. in the presence of a bismuth phosphomolybdate-based catalyst in the presence of small quantities of oxygen, has been reported. A reaction of this kind has been described in Patent FR-A-2,341,562 and its certificate of addition FR-A-2,418,223.

These references essentially teach the dehydration of N-ethylformamide to propionitrile, but make absolutely no mention of the formation of by-products such as ethylene.

However, it may be noted that experiments performed with N-tert-butylformamide give poor results with respect to selectivity.

In the context of the development of the present invention, attempts were made to prepare di-n-propylacetonitrile by the dehydration of N-(1-propyl-n-butyl)formamide according to the prior methods described above, that is to say employing a catalyst consisting of undoped silica, of silica doped with titanium chloride or alternatively of a bismuth phosphomolybdate.

In all cases, as a consequence of the breakage of C—N bonds, ethylenic by-products were obtained in quantities greater than 10%, capable of reaching, in some cases, more than 20%, as well as more than 2% of isomers of di-n-propylacetonitrile, namely 2-ethylhexanenitrile and 2-methylheptanenitrile.

For example, the dehydration of N-(1-propyl-n-butyl)formamide was performed using an undoped silica as catalyst by applying the process below:

13.5 cm³ of pelletized silica gel (2×3 mm), having the following characteristics:

| | |
|---|---|
| specific surface area | 320 m²/g |
| pore volume | 1.75 ml/g |
| pH of a 5% strength suspension | 6.0 |
| SiO₂ content | 99.6% |
| Al₂O₃ content | 0.15% |
| Na₂O content | 0.04% | are placed in the middle of a 200-cm³ tubular Pyrex glass reactor (diameter 2 cm, length 32 cm).

The reactor is placed in an electric oven, and the pretreatment of the catalyst is performed for 20 hours under a nitrogen flux (10 l/h) at 350° C., and 12 g (13.5 ml/h) of N-(1-propyl-n-butyl)formamide and 10 l/h of nitrogen are then introduced via the top of the reactor. The products formed are recovered at the bottom of the reactor by means of two double-walled containers, one maintained at 50° C. and the other at −10° C. Gas chromatographic analysis of the crude mixture of products obtained is performed periodically. After 7 hours' operation, it is found that the conversion of N-(1-propyl-n-butyl)formamide and the selectivity with respect to the products, expressed in % relative to the formamide converted, does not change.

The crude mixture then has the following composition:

| | |
|---|---|
| Heptenes | 22.5% |
| Di-n-propylmethylamine | 3.0% |
| Di-n-propylacetonitrile | 66.5% |
| 2-Ethylhexanenitrile | 1.9% |
| 2-Methylheptanenitrile | 0.5% |
| Unconverted N-(1-propyl-n-butyl)formamide | 5.6% |

Conversion of N-(1-propyl-n-butyl)formamide is hence 94.4% for a 66.5% yield of di-n-propylacetonitrile. In addition, a production of heptenes of more than 20% (double bond at the 1- or 2-position as minor components, at the 3-position predominant) and of isomers of di-n-propylacetonitrile of approximately 2.5% are observed.

Accordingly, the process thus described cannot be used for the future preparation of di-n-propylacetamide or di-n-propylacetic acid, the di-n-propylacetonitrile obtained being contaminated by an excessively large quantity of by-products. In effect, according to the pharmaceutical standards in force, di-n-propylacetamide or di-n-propylacetic acid cannot contain more than 0.4% of impurities.

It has now been found, unforeseeably, that it is possible to prepare di-n-propylacetonitrile according to a continuous process, by employing the high-temperature dehydration of N-(1-propyl-n-butyl)formamide in the presence of a catalyst based on silica doped by means of a basic element, while considerably reducing the formation of by-products.

Thus, di-n-propylacetonitrile is prepared according to the invention by heating N-(1-propyl-n-butyl)formamide of formula:

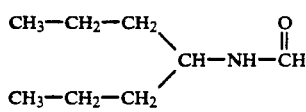

to a temperature of between 350° C. and 550° C., and preferably between 400° C. and 500° C., and in the absence of oxygen, in the presence of a catalyst consisting of a silica impregnated with 0.1 to 10% by weight, and preferably with 0.25 to 2% by weight, of alkali metal cations such as, for example, $Na^+$ or $K^+$, thereby yielding the desired compound.

The catalysts used in the process of the invention are prepared from silica gels having a specific surface area preferably of between 200 and 500 m$^2$/g, and a pore volume preferably of between 0.8 and 2.0 ml/g.

Silica gels of this type are commercially available, or may be prepared from aqueous solutions of sodium silicate by precipitation with ammonia solution.

These silica gels are then impregnated with alkali metal cations, that is to say brought in contact, at room temperature, with an aqueous solution of an alkali metal hydroxide or an alkali metal salt such as, for example, an alkali metal carbonate. The silica gels thus impregnated can then, after drying for 10 to 24 hours at 150°-200° C., be shaped by extrusion or pelletizing according to customary techniques.

Regeneration of the catalyst in question after a sufficiently long operating time, in order to enable its initial activity to be restored, is carried out by treatment under diluted oxygen at a temperature that permits combustion of the coke formed. A treatment of this type fully restores the activity and selectivity of this catalyst.

The catalytic dehydration of N-(1-propyl-n-butyl)-formamide is preferably performed according to a reaction in the gaseous phase on a fixed bed of catalyst at high temperature, generally 400° to 500° C. The use of such a reaction necessitates, at these temperatures, the absence of oxygen, which leads to successive decomposition reactions of the organic molecules present. It is accordingly necessary to perform the process of the invention under an inert gas such as nitrogen or argon.

Catalysts based on silica gel, used in the process of the invention, are of considerable value on account of the fact that they enable di-n-propylacetonitrile to be prepared in yields of the order of 80 to 85% while avoiding the production of heptenes, and while bringing the content of isomers of di-n-propylacetonitrile down to a value below 0.1%.

Accordingly, another subject of the invention relates to a catalyst for carrying out the process according to the invention, consisting of a silica impregnated with 0.1 to 10% by weight of alkali metal cations, as is described above.

N-(1-Propyl-n-butyl)formamide is a known product, described in Chimie Therapeutique, No. 5 pp. 388-391 (1972) as a compound difficult to prepare and unstable in nature since it changes with the passage of time.

It has been found, in the context of the present invention, that N-(1-propyl-n-butyl)formamide may be readily prepared by the action in the heated state, for example at a temperature of 130° to 150° C., of excess of an alkyl formate, such as ethyl formate, on di-n-propylmethylamine. In this way, a completely defined and pure compound is obtained in a yield of more than 95%, this compound being stable at room temperature.

As regards di-n-propylmethylamine, this is also a known compound according to Chimie Therapeutique, cited above. This amine may be obtained in an especially advantageous manner by the reaction of di-n-propylmethanol or di-n-propylacetone with ammonia and hydrogen in the presence of a nickel-based catalyst, for example Raney nickel, the reaction taking place at a temperature of between 150° and 180° C.

According to this process, a yield of di-n-propylmethylamine of more than 95% is obtained.

The following non-limiting examples illustrate the invention:

EXAMPLE 1

Preparation of di-n-propylacetonitrile

A) Di-n-propylmethylamine

A mixture consisting of di-n-propyl ketone/ammonia/hydrogen in the mole ratio 1:5:5 is passed at a pressure of $4.5 \times 10^5$ Pa through a tubular reactor (diameter: 2.5 cm; length: 60 cm) containing 50 cm$^3$ of nickel catalyst (55%) supported on kieselguhr. The hourly flow rate of di-n-propyl ketone is 25 cm$^3$/h and the temperature setting of the oven is 175° C.

The reaction effluent is recovered at the outlet of the reactor in a condenser maintained at 10° C.

Chromatographic analysis of the mixture shows that it consists of 97% of di-n-propylmethylamine, 1% of tri(di-n-propylamino)heptane and 1% of di-n-propyl ketone.

B) N-(1-Propyl-n-butyl)formamide

A mixture consisting of one mole of di-n-propylmethylamine and 4 moles of methyl formate is passed through a tubular reactor filled with glass beads (diameter: 2.5 cm; length: 60 cm) at a flow rate of 50 cm$^3$/h. The heated zone of the reactor corresponds to 100 cm$^3$.

A temperature of 150° C. is maintained in this portion of the reactor, and the reaction effluent is condensed at the outlet of the reactor in two containers in cascade, one maintained at 35° C. and the other at 0° C.

By analysis of the first condenser, a mixture of 98% of N-(1-propyl-n-butyl)formamide and 2% of di-n-propylmethylamine is obtained.

In the second condenser, a mixture of methanol and methyl formate is recovered.

C) Di-n-propylacetonitrile a) Catalyst 50 g of silica gel having the following characteristics:

| | |
|---|---|
| specific surface area | 320 m$^2$/g |
| pore volume | 1.75 ml/g |
| pH of a 5% strength suspension | 6.0 |
| SiO$_2$ content | 99.6% |
| Al$_2$O$_3$ content | 0.15% |
| Na$_2$O content | 0.04% | are impregnated in a conventional manner in a solution comprising 10.8 ml of 1 N sodium hydroxide and 150 ml of demineralized water. The solution is evaporated under vacuum at 70° C., and the silica impregnated with 0.54% of Na$^+$ thereby obtained is placed in the middle of a 200-cm$^3$ tubular Pyrex reactor (diameter 2 cm, length cm). The reactor is placed in an electric oven and the catalyst is then treated under a nitrogen flux (10 l/h) for 20 hours at 350° C.

b) Nitrile 12 g (13.5 ml/h) of N-(1-propyl-n-butyl)formamide and 10 l/h of nitrogen are then injected through a diffuser via the top of the reactor, and the temperature is brought to 500° C. After 7 hours' operation, the crude product obtained is recovered at the bottom of the reactor by means of two double-walled receivers, one maintained at 50° C. and the other at −10° C. During this operation, gas chromatographic analysis of the mixture of crude products obtained is performed periodically.

In this way, di-n-propylacetonitrile is obtained in crude form, that is to say a composition containing:

| | |
|---|---|
| Heptenes | 0% |
| Di-n-propylmethylamine | 4.3% |
| Di-n-propylacetonitrile | 78.3% |
| Isomers of di-n-propylacetonitrile | <0.1% |
| Unconverted N-(1-propyl-n-butyl)formamide | 17.4% |

After the di-n-propylmethylamine is separated off by acid washing and the di-n-propylacetonitrile is distilled off, the di-n-propylmethylamine can be recovered in order to restore the starting formamide and the unconverted N-(1-propyl-n-butyl)formamide, in order to recycle it in the dehydration reaction.

EXAMPLE 2

Preparation of di-n-propylacetonitrile a) N-(1-Propyl-n-butyl)formamide 600 g (5.06 moles) of di-n-propylmethylamine and 520 g (7.01 moles) of ethyl formate are introduced, while flushing with nitrogen, into a 1.5 l reactor equipped with a heating system, a stirrer, a thermometer and a condenser. The mixture is heated at 50° C. for 13 hours, and the crude reaction product is then concentrated in a rotary evaporator so as to remove the excess ethyl formate and the unreacted di-n-propylmethylamine. The residue thereby obtained is taken up with 2000 ml of diisopropyl ether, and the resulting mixture is washed successively with 3 times 200 ml of 10% strength aqueous hydrochloric acid and twice 200 ml of water. The organic phase is dried over sodium sulphate and concentrated in a rotary evaporator.

In this way, 656 g of N-(1-propyl-n-butyl)formamide, assaying at 98.6%, are obtained.

This compound may be obtained analytically pure by distillation.

B.p 86° C. (0.66 Pa).

Percentage analysis %:

| | C | H | N |
|---|---|---|---|
| Calculated | 67.09 | 11.96 | 9.78 |
| Found | 66.74 | 12.22 | 9.69 |

IR spectrum (film):
Associated NH: 3300 cm$^{-1}$ (m) 3060 cm$^{-1}$ (m),
HC=O: 2860 cm$^{-1}$ (m),
C=O: 1680 cm$^{-1}$ (f).

b) Di-n-propylacetonitrile

The process described in Example 1 is used, employing a catalyst based on the same silica gel, but impregnated on this occasion with 0.8% of K$^+$, supplied in the form of potassium hydroxide, prepared under the same conditions as in Example 1.

After 12 hours' operation, crude di-n-propylacetonitrile is obtained, namely a composition containing:

| | |
|---|---|
| Heptenes | 0% |
| Di-n-propylmethylamine | 3.1% |
| Di-n-propylacetonitrile | 83.1% |
| Isomers of di-n-propylacetonitrile | <0.1% |
| Unconverted N-(1-propyl-n-butyl)formamide | 13.8% |

EXAMPLE 3

Preparation of di-n-propylacetonitrile

The process described in Example 1 is used, employing a catalyst based on silica gel resulting from the precipitation of sodium silicate. This gel, having a specific surface area equal to 260 m$^2$/g and a pore volume equal to 1.08 ml/g, is subsequently impregnated with 2.14% of Na$^+$.

Crude di-n-propylacetonitrile, namely the following composition:

| | |
|---|---|
| Heptenes | 2.1% |
| Di-n-propylmethylamine | 4.8% |
| Di-n-propylacetonitrile | 64.2% |
| Isomers of di-n-propylacetonitrile | <0.1% |
| Unconverted N-(1-propyl-n-butyl)formamide | 28.8% | is thereby obtained at 450° C. after 92 hours' operation.

The catalyst is then subjected to a regeneration for 4 hours at 450° C. under a gaseous mixture composed of 99.5% of nitrogen and 0.5% of oxygen at a flow rate of 13.5 l/h, and 16 hours under a 1.5%:98.5% oxygen/nitrogen mixture. After this treatment, the injection of N-(1-propyl-n-butyl)formamide in nitrogen is resumed and, after 155 hours, crude di-n-propylacetonitrile is obtained, that is to say a composition of formula:

| | |
|---|---|
| Heptenes | 0% |
| Di-n-propylmethylamine | 4.5% |
| Di-n-propylacetonitrile | 71.6% |
| Isomers of di-propylacetonitrile | <0.1% |
| Unconverted N-(1-propyl-n-butyl)formamide | 23.9% |

A regeneration of the catalyst is then performed according to the same procedure as above. After resumption of the injection of the reactants under the same conditions as above (temperature: 450° C.), crude di-n-propylacetonitrile, namely the following composition:

| | |
|---|---|
| Heptenes | 0% |
| Di-n-propylmethylamine | 8.2% |
| Di-n-propylacetonitrile | 85.5% |
| Isomers of di-n-propylacetonitrile | <0.1% |
| Unconverted N-(1-propyl-n-butyl)formamide | 6.2% | is obtained after 7 hours' operation.

We claim:

1. Process for preparing di-n-propylacetonitrile of the formula:

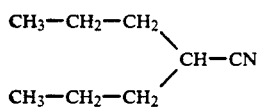

comprising heating in the absence of oxygen N-(1-propyl-n-butyl)formamide of the formula:

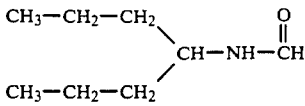

to a temperature of between 350° C. and 550° C., in the presence of a catalyst obtained by the impregnation with 0.54% to 2.14% by weight of alkali metal cations of a silica gel containing at least 99.6 of silica and having a specific surface area of between 260 m²/g and 320 m²/g and a pore volume between 1.08 ml/g and 1.75 ml/g, to obtain the desired compound.

2. Process according to claim 1, wherein the temperature is between 400° and 500° C.

3. Process according to claim 1, wherein the catalyst is obtained by the impregnation of a silica gel with an aqueous solution of an alkali metal hydroxide or an alkali metal salt.

4. Process according to claim 1, wherein the alkali metal is sodium or potassium.

5. Process according to claim 1, wherein the specific surface area is 320 m²/g and the pore volume is 1.75 ml/g.

6. Process according to claim 1, wherein the specific area is 260 m²/g and the pore volume is 1.08 ml/g.

* * * * *